United States Patent
Miller et al.

(10) Patent No.: US 9,561,104 B2
(45) Date of Patent: Feb. 7, 2017

(54) ACTIVELY-ENGAGEABLE MOVEMENT-RESTRICTION MECHANISM FOR USE WITH AN ANNULOPLASTY STRUCTURE

(71) Applicant: VALTECH CARDIO, LTD., Or Yehuda (IL)

(72) Inventors: Eran Miller, Moshav Beit Elazari (IL); Amir Gross, Moshav Mazor (IL); Oz Cabiri, Macabim-Reut (IL); Iftah Beinart, Hod Hasharon (IL); Aviram Baum, Tel Aviv (IL)

(73) Assignee: VALTECH CARDIO, LTD., Or Yehuda (IL)

( * ) Notice: Subject to any disclaimer, the term of this patent is extended or adjusted under 35 U.S.C. 154(b) by 1012 days.

(21) Appl. No.: 13/740,582

(22) Filed: Jan. 14, 2013

(65) Prior Publication Data
US 2013/0131792 A1 May 23, 2013

Related U.S. Application Data

(62) Division of application No. 12/706,868, filed on Feb. 17, 2010, now Pat. No. 8,353,956.
(Continued)

(51) Int. Cl.
*A61F 2/82* (2013.01)
*A61F 2/24* (2006.01)

(52) U.S. Cl.
CPC ........... *A61F 2/2442* (2013.01); *A61F 2/2448* (2013.01); *A61F 2250/0004* (2013.01)

(58) Field of Classification Search
CPC .................................... A61F 2/82; A61F 2/24
See application file for complete search history.

(56) References Cited

U.S. PATENT DOCUMENTS

| | | |
|---|---|---|
| 3,656,185 A | 4/1972 | Carpentier |
| 4,042,979 A | 8/1977 | Angell |
| | (Continued) | |

FOREIGN PATENT DOCUMENTS

| | | |
|---|---|---|
| EP | 0614342 A1 | 9/1994 |
| EP | 1006905 A1 | 6/2000 |
| | (Continued) | |

OTHER PUBLICATIONS

An Office Action dated Oct. 2, 2013, which issued during the prosecution of U.S. Appl. No. 13/167,492.
(Continued)

*Primary Examiner* — Matthew Schall
(74) *Attorney, Agent, or Firm* — Ladas & Parry LLP

(57) ABSTRACT

A method is provided, including providing an implant shaped to define a lumen and a flexible strip disposed at least in part within the lumen, and a plurality of recesses, the implant including a locking mechanism to which first and second ends of the strip are coupled such that the strip defines a closed loop which shortens when the first end is advanced through the locking mechanism in a first direction, and expands when the first end is advanced in a second opposite direction; advancing the first end in first and second opposing directions with respect to the second end; maintaining a recess-engaging portion in a position in which the recess-engaging portion is not disposed in any of the recesses during the advancing; and restricting the advancing by facilitating active positioning of the recess-engaging portion in one of the recesses. Other embodiments are also described.

5 Claims, 6 Drawing Sheets

Related U.S. Application Data

(60) Provisional application No. 61/207,908, filed on Feb. 17, 2009.

(56) References Cited

U.S. PATENT DOCUMENTS

| | | |
|---|---|---|
| 4,118,805 A | 10/1978 | Reimels |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,061,277 A | 10/1991 | Carpentier et al. |
| 5,104,407 A | 4/1992 | Lam et al. |
| 5,108,420 A | 4/1992 | Marks |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,450,860 A | 9/1995 | O'Connor |
| 5,474,518 A | 12/1995 | Farrer Velazquez |
| 5,477,856 A | 12/1995 | Lundquist |
| 5,593,424 A | 1/1997 | Northrup, III |
| 5,669,919 A | 9/1997 | Sanders et al. |
| 5,674,279 A | 10/1997 | Wright et al. |
| 5,716,370 A | 2/1998 | Williamson, IV et al. |
| 5,730,150 A | 3/1998 | Peppel et al. |
| 5,749,371 A | 5/1998 | Zadini et al. |
| 5,810,882 A | 9/1998 | Bolduc et al. |
| 5,824,066 A | 10/1998 | Gross |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,961,440 A | 10/1999 | Schweich, Jr. et al. |
| 5,961,539 A | 10/1999 | Northrup, III et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,401 A | 6/2000 | Gardiner et al. |
| 6,102,945 A | 8/2000 | Campbell |
| 6,110,200 A | 8/2000 | Hinnenkamp |
| 6,143,024 A | 11/2000 | Campbell et al. |
| 6,165,119 A | 12/2000 | Schweich, Jr. et al. |
| 6,183,411 B1 | 2/2001 | Mortier et al. |
| 6,187,040 B1 | 2/2001 | Wright |
| 6,251,092 B1 | 6/2001 | Qin et al. |
| 6,319,281 B1 | 11/2001 | Patel |
| 6,332,893 B1 | 12/2001 | Mortier et al. |
| 6,406,420 B1 | 6/2002 | McCarthy et al. |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,524,338 B1 | 2/2003 | Gundry |
| 6,537,314 B2 | 3/2003 | Langberg et al. |
| 6,547,801 B1 | 4/2003 | Dargent et al. |
| 6,564,805 B2 | 5/2003 | Garrison et al. |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,709,385 B2 | 3/2004 | Forsell |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,786,924 B2 | 9/2004 | Ryan et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,862 B2 | 7/2006 | Vidlund et al. |
| 7,087,064 B1 | 8/2006 | Hyde |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,226,647 B2 | 6/2007 | Kasperchik et al. |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,316,710 B1 | 1/2008 | Cheng et al. |
| 7,329,280 B2 | 2/2008 | Bolling et al. |
| 7,335,213 B1 | 2/2008 | Hyde et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,530,995 B2 | 5/2009 | Quijano et al. |
| 7,549,983 B2 | 6/2009 | Roue et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,704,277 B2 | 4/2010 | Zakay et al. |
| 7,736,388 B2 | 6/2010 | Goldfarb et al. |

(56) References Cited

U.S. PATENT DOCUMENTS

| | | |
|---|---|---|
| 7,753,924 B2 | 7/2010 | Starksen et al. |
| 7,871,368 B2 | 1/2011 | Zollinger et al. |
| 7,993,368 B2 | 8/2011 | Gambale et al. |
| 8,052,592 B2 | 11/2011 | Goldfarb et al. |
| 8,070,804 B2 | 12/2011 | Hyde et al. |
| 8,123,800 B2 | 2/2012 | McCarthy et al. |
| 8,123,801 B2 | 2/2012 | Milo |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,187,299 B2 | 5/2012 | Goldfarb et al. |
| 8,202,315 B2 | 6/2012 | Hlavka et al. |
| 8,226,711 B2 | 7/2012 | Mortier et al. |
| 8,241,351 B2 | 8/2012 | Cabiri |
| 8,252,050 B2 | 8/2012 | Maisano et al. |
| 8,287,591 B2 | 10/2012 | Keidar et al. |
| 8,303,608 B2 | 11/2012 | Goldfarb et al. |
| 8,343,173 B2 | 1/2013 | Starksen et al. |
| 8,343,174 B2 | 1/2013 | Goldfarb et al. |
| 8,349,002 B2 | 1/2013 | Milo |
| 8,353,956 B2 | 1/2013 | Miller et al. |
| 8,382,829 B1 | 2/2013 | Call et al. |
| 8,388,680 B2 | 3/2013 | Starksen et al. |
| 8,393,517 B2 | 3/2013 | Milo |
| 8,460,370 B2 | 6/2013 | Zakay et al. |
| 8,460,371 B2 | 6/2013 | Hlavka et al. |
| 8,475,491 B2 | 7/2013 | Milo |
| 8,518,107 B2 | 8/2013 | Tsukashima et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,628,571 B1 | 1/2014 | Hacohen |
| 8,641,727 B2 | 2/2014 | Starksen et al. |
| 8,652,202 B2 | 2/2014 | Alon et al. |
| 8,715,342 B2 | 5/2014 | Zipory et al. |
| 8,728,097 B1 | 5/2014 | Sugimoto et al. |
| 8,734,467 B2 | 5/2014 | Miller et al. |
| 8,740,920 B2 | 6/2014 | Goldfarb et al. |
| 8,778,021 B2 | 7/2014 | Cartledge |
| 8,790,367 B2 | 7/2014 | Nguyen et al. |
| 8,795,298 B2 | 8/2014 | Hernlund et al. |
| 8,808,371 B2 | 8/2014 | Cartledge |
| 8,845,717 B2 | 9/2014 | Khairkhahan et al. |
| 8,845,723 B2 | 9/2014 | Spence et al. |
| 8,852,272 B2 | 10/2014 | Gross et al. |
| 8,858,623 B2 | 10/2014 | Miller et al. |
| 8,864,822 B2 | 10/2014 | Spence et al. |
| 8,888,843 B2 | 11/2014 | Khairkhahan et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,932,348 B2 | 1/2015 | Solem et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 9,011,530 B2 | 4/2015 | Reich et al. |
| 9,017,399 B2 | 4/2015 | Gross et al. |
| 9,119,719 B2 | 9/2015 | Zipory et al. |
| 9,125,632 B2 | 9/2015 | Loulmet et al. |
| 9,173,646 B2 | 11/2015 | Fabro |
| 9,180,005 B1 | 11/2015 | Lashinski et al. |
| 9,226,825 B2 | 1/2016 | Starksen et al. |
| 2001/0021874 A1 | 9/2001 | Carpentier et al. |
| 2001/0044656 A1 | 11/2001 | Williamson, IV et al. |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0151961 A1 | 10/2002 | Lashinski et al. |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |
| 2003/0050693 A1 | 3/2003 | Quijano et al. |
| 2003/0078465 A1 | 4/2003 | Pai et al. |
| 2003/0105519 A1 | 6/2003 | Fasol et al. |
| 2003/0167062 A1 | 9/2003 | Gambale et al. |
| 2003/0199974 A1 | 10/2003 | Lee et al. |
| 2003/0229395 A1 | 12/2003 | Cox |
| 2003/0233142 A1 | 12/2003 | Morales et al. |
| 2004/0024451 A1 | 2/2004 | Johnson et al. |
| 2004/0049207 A1 | 3/2004 | Goldfarb et al. |
| 2004/0092962 A1 | 5/2004 | Thornton et al. |
| 2004/0122448 A1 | 6/2004 | Levine |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133274 A1 | 7/2004 | Webler et al. |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0181287 A1 | 9/2004 | Gellman |
| 2004/0186566 A1 | 9/2004 | Hindrichs et al. |
| 2004/0236419 A1 | 11/2004 | Milo |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0288776 A1 | 12/2005 | Shaoulian et al. |
| 2005/0288781 A1 | 12/2005 | Moaddeb et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0025787 A1 | 2/2006 | Morales et al. |
| 2006/0025855 A1 | 2/2006 | Lashinski et al. |
| 2006/0041319 A1 | 2/2006 | Taylor et al. |
| 2006/0058871 A1 | 3/2006 | Zakay et al. |
| 2006/0069429 A1 | 3/2006 | Spence et al. |
| 2006/0085012 A1 | 4/2006 | Dolan |
| 2006/0095009 A1 | 5/2006 | Lampropoulos et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0161265 A1 | 7/2006 | Levine et al. |
| 2006/0195134 A1 | 8/2006 | Crittenden |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0282161 A1 | 12/2006 | Huynh et al. |
| 2006/0287716 A1 | 12/2006 | Banbury et al. |
| 2007/0016287 A1 | 1/2007 | Cartledge et al. |
| 2007/0027533 A1 | 2/2007 | Douk |
| 2007/0027536 A1 | 2/2007 | Mihaljevic et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |

(56) References Cited

U.S. PATENT DOCUMENTS

| | | |
|---|---|---|
| 2007/0080188 A1 | 4/2007 | Spence et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0282375 A1 | 12/2007 | Hindrichs et al. |
| 2007/0282429 A1 | 12/2007 | Hauser et al. |
| 2008/0004697 A1 | 1/2008 | Lichtenstein et al. |
| 2008/0027483 A1 | 1/2008 | Cartledge et al. |
| 2008/0035160 A1 | 2/2008 | Woodson et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0086203 A1 | 4/2008 | Roberts |
| 2008/0097523 A1 | 4/2008 | Bolduc et al. |
| 2008/0140116 A1 | 6/2008 | Bonutti |
| 2008/0177382 A1 | 7/2008 | Hyde et al. |
| 2008/0195126 A1 | 8/2008 | Solem |
| 2008/0228265 A1 | 9/2008 | Spence et al. |
| 2008/0262609 A1 | 10/2008 | Gross et al. |
| 2008/0288044 A1 | 11/2008 | Osborne |
| 2009/0043153 A1 | 2/2009 | Zollinger et al. |
| 2009/0054969 A1 | 2/2009 | Salahieh et al. |
| 2009/0105816 A1 | 4/2009 | Olsen et al. |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1 | 7/2009 | Milo |
| 2009/0222083 A1 | 9/2009 | Nguyen et al. |
| 2009/0248148 A1 | 10/2009 | Shaolian et al. |
| 2009/0259307 A1 | 10/2009 | Gross et al. |
| 2009/0287304 A1 | 11/2009 | Dahlgren et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023117 A1 | 1/2010 | Yoganathan et al. |
| 2010/0049313 A1 | 2/2010 | Alon et al. |
| 2010/0094248 A1 | 4/2010 | Nguyen et al. |
| 2010/0130992 A1 | 5/2010 | Machold et al. |
| 2010/0152845 A1 | 6/2010 | Bloom et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0198347 A1 | 8/2010 | Zakay et al. |
| 2010/0211166 A1 | 8/2010 | Miller et al. |
| 2010/0217382 A1 | 8/2010 | Chau et al. |
| 2010/0234935 A1 | 9/2010 | Bashiri et al. |
| 2010/0249920 A1 | 9/2010 | Bolling et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0324598 A1 | 12/2010 | Anderson |
| 2011/0004298 A1 | 1/2011 | Lee et al. |
| 2011/0029066 A1 | 2/2011 | Gilad et al. |
| 2011/0071626 A1 | 3/2011 | Wright et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0184510 A1 | 7/2011 | Maisano et al. |
| 2011/0190879 A1 | 8/2011 | Bobo et al. |
| 2011/0202130 A1 | 8/2011 | Cartledge et al. |
| 2011/0264208 A1 | 10/2011 | Duffy et al. |
| 2011/0276062 A1 | 11/2011 | Bolduc |
| 2011/0282361 A1 | 11/2011 | Miller et al. |
| 2012/0022557 A1 | 1/2012 | Cabiri et al. |
| 2012/0022644 A1 | 1/2012 | Reich et al. |
| 2012/0035712 A1 | 2/2012 | Maisano et al. |
| 2012/0078355 A1 | 3/2012 | Zipory et al. |
| 2012/0089022 A1 | 4/2012 | House et al. |
| 2012/0109155 A1 | 5/2012 | Robinson et al. |
| 2012/0123531 A1 | 5/2012 | Tsukashima et al. |
| 2012/0136436 A1 | 5/2012 | Cabiri et al. |
| 2012/0158021 A1 | 6/2012 | Morrill |
| 2012/0191182 A1 | 7/2012 | Hauser et al. |
| 2012/0197388 A1 | 8/2012 | Khairkhahan et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296417 A1 | 11/2012 | Hill et al. |
| 2012/0296419 A1 | 11/2012 | Richardson et al. |
| 2012/0310330 A1 | 12/2012 | Buchbinder et al. |
| 2012/0330410 A1 | 12/2012 | Hammer et al. |
| 2012/0330411 A1 | 12/2012 | Gross et al. |
| 2013/0023758 A1 | 1/2013 | Fabro |
| 2013/0116780 A1 | 5/2013 | Miller et al. |
| 2013/0131791 A1 | 5/2013 | Hlavka et al. |
| 2013/0190863 A1 | 7/2013 | Call et al. |
| 2013/0190866 A1 | 7/2013 | Zipory et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0304093 A1 | 11/2013 | Serina et al. |
| 2013/0325118 A1 | 12/2013 | Cartledge |
| 2014/0088368 A1 | 3/2014 | Park |
| 2014/0094826 A1 | 4/2014 | Sutherland et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0243859 A1 | 8/2014 | Robinson |
| 2014/0243894 A1 | 8/2014 | Groothuis et al. |
| 2014/0275757 A1 | 9/2014 | Goodwin et al. |
| 2014/0303649 A1 | 10/2014 | Nguyen et al. |
| 2014/0303720 A1 | 10/2014 | Sugimoto et al. |
| 2014/0309730 A1 | 10/2014 | Alon et al. |
| 2014/0343668 A1 | 11/2014 | Zipory et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0127097 A1 | 5/2015 | Neumann et al. |
| 2015/0272734 A1 | 10/2015 | Sheps et al. |
| 2015/0351906 A1 | 12/2015 | Hammer et al. |

FOREIGN PATENT DOCUMENTS

| | | |
|---|---|---|
| EP | 0954257 B1 | 8/2000 |
| EP | 1258437 A1 | 11/2002 |
| EP | 0871417 B1 | 10/2003 |
| EP | 1266641 B1 | 10/2004 |
| EP | 1034753 B1 | 2/2005 |
| EP | 1562522 B1 | 12/2008 |
| EP | 1258232 B1 | 1/2009 |
| EP | 1420723 B1 | 1/2009 |
| EP | 1903991 B1 | 9/2009 |
| EP | 1418865 B1 | 10/2009 |
| EP | 2119399 A1 | 11/2009 |

(56) References Cited

FOREIGN PATENT DOCUMENTS

| | | |
|---|---|---|
| EP | 1531762 B1 | 4/2010 |
| EP | 2273928 A2 | 1/2011 |
| EP | 1450733 B1 | 2/2011 |
| EP | 2445417 A2 | 5/2012 |
| EP | 1861045 B1 | 3/2015 |
| EP | 1465555 B1 | 5/2015 |
| WO | 92/05093 A1 | 4/1992 |
| WO | 93/10714 A1 | 6/1993 |
| WO | 96/39963 A1 | 12/1996 |
| WO | 96/40344 A1 | 12/1996 |
| WO | 97/01369 A1 | 1/1997 |
| WO | 98/46149 A1 | 10/1998 |
| WO | 00/22981 A1 | 4/2000 |
| WO | 01/26586 A1 | 4/2001 |
| WO | 01/56457 A1 | 8/2001 |
| WO | 02/085250 A2 | 10/2002 |
| WO | 02/085251 A1 | 10/2002 |
| WO | 02/085252 A1 | 10/2002 |
| WO | 03/028558 A2 | 4/2003 |
| WO | 03/049647 A1 | 6/2003 |
| WO | 03/105667 A2 | 12/2003 |
| WO | 2005/021063 A2 | 3/2005 |
| WO | 2005/046488 A2 | 5/2005 |
| WO | 2006/012013 A2 | 2/2006 |
| WO | 2006/086434 A1 | 8/2006 |
| WO | 2006/097931 A2 | 9/2006 |
| WO | 2006/105084 A2 | 10/2006 |
| WO | 2006/116558 A2 | 11/2006 |
| WO | 2007/136783 A2 | 11/2007 |
| WO | 2008/068756 A2 | 6/2008 |
| WO | 2010/004546 A1 | 1/2010 |
| WO | 2010/044851 A1 | 4/2010 |
| WO | 2010/073246 A2 | 7/2010 |
| WO | 2010/128502 A1 | 11/2010 |
| WO | 2010/128503 A2 | 11/2010 |
| WO | 2011/051942 A1 | 5/2011 |
| WO | 2011/067770 A1 | 6/2011 |
| WO | 2011/089601 A1 | 7/2011 |
| WO | 2012/014201 A2 | 2/2012 |
| WO | 2012/068541 A2 | 5/2012 |
| WO | 2012/176195 A2 | 12/2012 |
| WO | 2013/069019 A2 | 5/2013 |
| WO | 2013/088327 A1 | 6/2013 |
| WO | 2014/195786 A2 | 12/2014 |

OTHER PUBLICATIONS

An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
An Office Action dated Dec. 19, 2013, which issued during the prosecution of U.S. Appl. No. 14/027,934.
European Search Report dated Mar. 23, 2015; Appln. No. 09 834 225.6-1662.
Extended European Search Report dated Mar. 23, 2015; Appln. No. 11792047.0 - 1506/2575686 PCT/IL2011000446.
European Search Report dated Apr. 29, 2015; EP14200202.
International Search Report and Written Opinion dated May 12, 2015; PCT/IL2014/050914.
USPTO NFOA dated Mar. 24, 2011 in connection with U.S. Appl. No. 12/996,954.
USPTO FOA dated Apr. 2, 2015 in connection with U.S. Appl. No. 14/027,934.
USPTO RR dated May 28, 2015 in connection with U.S. Appl. No. 14/128,756.
USPTO NOA mailed Jun. 23, 2014 in connection with U.S. Appl. No. 12/548,991.
USPTO NFOA dated Aug. 26, 2014 in connection with U.S. Appl. No. 13/167,444.
USPTO NFOA dated Jun. 10, 2014 in connection with U.S. Appl. No. 13/167,492.
USPTO NOA mailed Jun. 25, 2014 in connection with U.S. Appl. No. 13/666,262.
International Search Report and Written Opinion both dated Jan. 25, 2016; PCT/IL2015/051027.
USPTO NFOA dated Jan. 5, 2016 in connection with U.S. Appl. No. 14/027,934.
USPTO FOA dated Jan. 5, 2016 in connection with U.S. Appl. No. 14/084,426.
USPTO FOA dated Jan. 6, 2016 in connection with U.S. Appl. No. 14/128,756.
USPTO NFOA dated Jan. 4, 2016 in connection with U.S. Appl. No. 14/589,100.
USPTO NFOA dated May 3, 2016 in connection with U.S. Appl. No. 13/319,030.
USPTO NFOA dated May 11, 2016 in connection with U.S. Appl. No. 14/128,756.
USPTO NFOA dated Apr. 8, 2016 in connection with U.S. Appl. No. 14/141,228.
USPTO NFOA dated May 23, 2016 in connection with U.S. Appl. No. 14/209,171.
USPTO NFOA dated Apr. 7, 2016 in connection with U.S. Appl. No. 14/242,151.
USPTO NFOA dated Jun. 14, 2016 in connection with U.S. Appl. No. 14/273,155.
USPTO NFOA dated Jun. 17, 2016 in connection with U.S. Appl. No. 14/357,040.
USPTO FOA dated May 4, 2016 in connection with U.S. Appl. No. 14/589,100.
USPTO Supplemental Notice of Allowance dated May 6, 2016 in connection with U.S. Appl. No. 14/667,090.
USPTO NOA mailed Apr. 12, 2016 in connection with U.S. Appl. No. 14/667,090.
Third Chinese Office Action in English dated Jul. 17, 2015; Appln. No. 201080059948.4.
EPO Office Action dated Jun. 11, 2015; Appln. No. 11 811 934.6.
USPTO NOA mailed Jul. 30, 2015 in connection with U.S. Appl. No. 13/319,007.
USPTO FOA dated Jun. 18, 2015 in connection with U.S. Appl. No. 13/319,030.
USPTO NFOA dated Aug. 7, 2015 in connection with U.S. Appl. No. 14/128,756.
USPTO NFOA dated Jun. 18, 2015 in connection with U.S. Appl. No. 14/551,951.
USPTO NFOA dated Sep. 29, 2014 in connection with U.S. Appl. No. 13/504,870.
USPTO NFOA dated Oct. 14, 2014 in connection with U.S. Appl. No. 13/319,030.
Extended European Search Report dated Sep. 25, 2015, Appln. 09794095.1-1651/2296744 PCT/IL2009000593.
European Patent Office Communication dated Nov. 4, 2015; Appln. No. 10 772 091.4-1662.
European Patent Office Communication dated Nov. 16, 2015; Appln. No. 10 826 224.7-1654.
English Translation of Office Action dated Nov. 24, 2015; Israel Patent Appln. No. 223448.
USPTO NFOA dated Oct. 1, 2015 in connection with U.S. Appl. No. 14/141,228.
USPTO NFOA dated Oct. 5, 2015 in connection with U.S. Appl. No. 14/246,417.
USPTO NOA mailed Nov. 17, 2015 in connection with U.S. Appl. No. 14/486,226.
Robert S. Dieter, MD; "Percutaneous valve repair: Update on mitral regurgitation and endovascular approaches to the mitral valve" Applications in Imaging, Cardiac Interventions, Supported by an educational grant from Amersham Health, pp. 11-14 (2003).
John A. Odell, et al; "Early Results of a Simplified Method of Mitral Valve Annuloplasty", Presented at the American Heart Association 67th Scientific Sessions, Dallas, TX, Nov. 14-17, 1994; Circulation © 1995, vol. 92, pp. 150-154.
S. O'Reilly, et al; "Heart Valve Surgery Pushes the Envelope", Medtech Insight, vol. 8, Issue 3, 73, 99-108; Mar. 2006.

(56) References Cited

OTHER PUBLICATIONS

Abdul J. Tajik, M.D., et al; "Two-Dimensional Real-Time Ultrasonic Imaging of the Heart and Great Vessels", Mayo Clinic Proceedings, vol. 53, Rochester, MN, May 1978, pp. 271-303.
C. Paul Swain, MD, et al; "An endoscopically deliverable tissue-transfixing device for securing biosensors in the gastrointestinal tract", Gastrointestinal Endoscopy, vol. 40, No. 6, pp. 730-734; Nov. 1994.
Supplementary European Search Report; dated Mar. 28, 2013; EP 10 77 2091.4.
International Search Report dated Jun. 10, 2010; PCT/IL09/01209.
International Search Report dated May 19, 2011; PCT/IL2011/00064.
International Preliminary Report on Patentability dated Jun. 29, 2011; PCT/IL2009/001209.
International Preliminary Report on Patentability dated Nov. 9, 2011; PCT/IL2010/000358.
International Preliminary Report on Patentability dated Jan. 29, 2013; PCT/IL2011/000600.
Search Report and Written Opinion dated Sep. 8, 2009, PCT/IL09/00593.
Search Report and Written Opinion dated Aug. 17, 2010, PCT/IL10/00357.
Search Report and Written Opinon dated Nov. 8, 2010, PCT/IL2010/000358.
Search Report and Written Opinion dated Dec. 6, 2012; PCT/IL2012/000250.
Search Report and Written Opinion dated Feb. 2, 2012; PCT/IL2011/000600.
Search Report and Written Opinion dated Feb. 22, 2013; PCT/IL2012/050451.
U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.
U.S. Appl. No. 61/557,082, filed Nov. 8, 2011.
USPTO NFOA dated Aug. 4, 2010 in connection with U.S. Appl. No. 12/341,960.
USPTO RR dated Jul. 12, 2011 in connection with U.S. Appl. No. 12/437,103.
USPTO NFOA dated Sep. 28, 2011 in connection with U.S. Appl. No. 12/437,103.
USPTO NFOA dated Jun. 13, 2012 in connection with U.S. Appl. No. 12/437,103.
USPTO NFOA dated Apr. 6, 2010 in connection with U.S. Appl. No. 12/484,512.
USPTO NFOA dated May 6, 2013 in connection with U.S. Appl. No. 12/689,693.
USPTO RR dated Jan. 23, 2012 in connection with U.S. Appl. No. 12/692,061.
USPTO OA Summary dated May 5, 2011 in connection with U.S. Appl. No. 12/706,868.
USPTO OA Summary dated May 19, 2011 in connection with U.S. Appl. No. 12/706,868.
USPTO NFOA dated Sep. 1, 2011 in connection with U.S. Appl. No. 12/706,868.
USPTO FOA dated May 30, 2012 in connection with U.S. Appl. No. 12/706,868.
USPTO NOA mailed Sep. 18, 2012 in connection with U.S. Appl. No. 12/706,868.
USPTO RR dated May 1, 2012 in connection with U.S. Appl. No. 12/843,412.
USPTO NFOA dated Jul. 20, 2012 in connection with U.S. Appl. No. 12/843,412.
USPTO NFOA dated Mar. 27, 2013 in connection with U.S. Appl. No. 12/843,412.
USPTO NFOA dated Feb. 12, 2013 in connection with U.S. Appl. No. 12/926,673.
USPTO NFOA dated Feb. 4, 2013 in connection with U.S. Appl. No. 13/141,606.
USPTO NFOA dated Jun. 7, 2013 in connection with U.S. Appl. No. 13/141,606.
USPTO NFOA dated Jan. 17, 2013 in connection with U.S. Appl. No. 13/167,444.
USPTO NFOA dated Apr. 1, 2013 in connection with U.S. Appl. No. 13/167,476.
USPTO NFOA dated Feb. 14, 2013 in connection with U.S. Appl. No. 13/167,492.
A. Ahmadi, et al; "Hemodynamic Changes Following Experimental Production and Correction of Acute Mitral Regurgitation with an Adjustable Ring Prosthesis", Thorac Cardiovasc Surg. Dec. 1988;36(6):313-9.
Ali Ahmadi, et al; "Percutaneously Adjustable Pulmonary Artery Band", The Annals of Thoracic Surgery; Dec. 1995, vol. 60, Supplement 3; pp. S520-S522.
Renato S. Assad; "Adjustable Pulmonary Artery Banding", Chapter 10 Open Access; Published Feb. 26, 2014; DOI:10.5772/57117; 32 pages.
S. Dabritz, et al; "Experience With an Adjustable Pulmonary Artery Banding Device in Two Cases: Initial Success-Midterm Failure", Thorac Cardiovasc Curg. Feb. 1999;47(1):51-2.
Daniel S. Elliott, et al; "An Implantable Mechanical Urinary Sphincter: A New Nonhydraulic Design Concept", Urology, Dec. 1998; 52(6): pp.1151-1154.
Sang C. Park, et al; "A Percutaneously adjustable device for banding of the pulmonary trunk", International Journal of Cardiology, 9; Dec. 1985(4):477-84.
Orvar Swenson; "Internal Device for Control of Urinary Incontinence", Journal of Pediatric Surgery, vol. 7, No. 5 (Oct.-Nov.) 1972; pp. 542-545.
Invitation to Pay Additional Fees dated Aug. 18, 2016; issued during prosecution of PCT/IL2016/050433.
Extended European Search Report dated Jul. 15, 2016; Appln. No. 13849947.0-1654/2911594; PCT/IL2013050860.
USPTO FOA dated Jul. 20, 2018 in connection with U.S. Appl. No. 14/246,417.

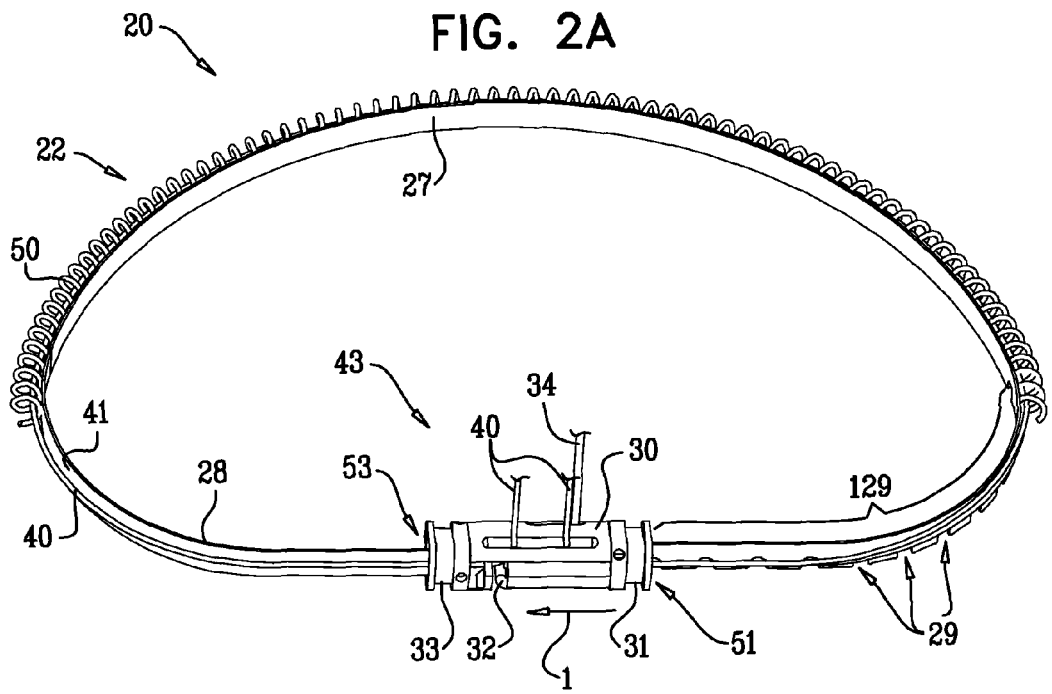
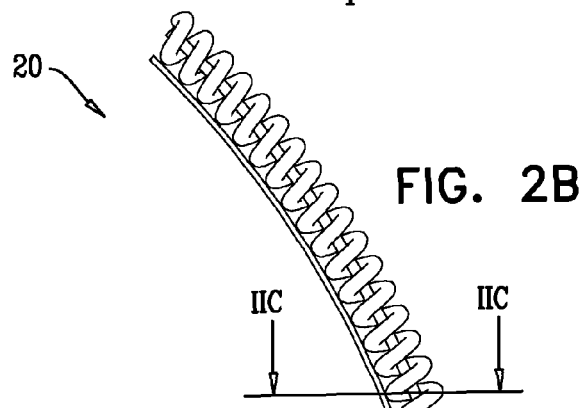
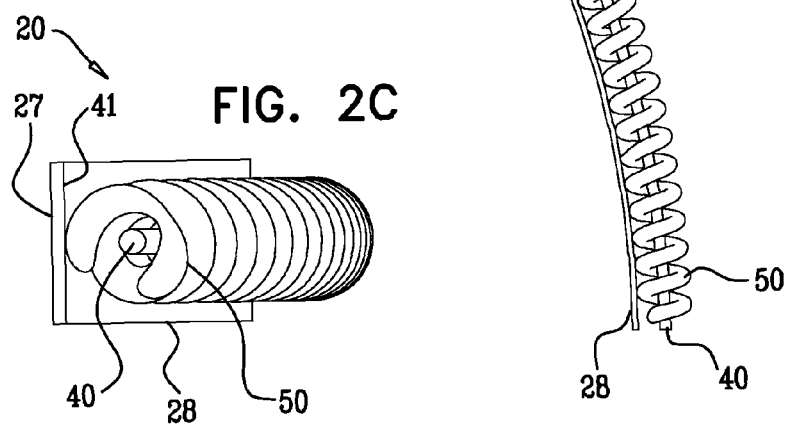

ACTIVELY-ENGAGEABLE MOVEMENT-RESTRICTION MECHANISM FOR USE WITH AN ANNULOPLASTY STRUCTURE

CROSS-REFERENCES TO RELATED APPLICATIONS

The present application claims the priority from U.S. Provisional Patent Application 61/207,908 to Miller et al., entitled, "Actively-engageable movement-restriction mechanism for use with an annuloplasty structure," filed on Feb. 17, 2009, which is incorporated herein by reference.

FILED OF THE INVENTION

Some applications of the present invention relate in general to valve repair. More specifically, some applications of the present invention relate to repair of a mitral valve of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publications 2004/0260393 to Rahdert et al. and 2004/0127982 to Machold et al. describe techniques using an implant that is sized and configured to attach in, on, or near the annulus of a dysfunctional heart valve. In use, the implant extends either across the minor axis of the annulus, or across the major axis of the annulus, or both. The implant is described as restoring to the heart valve annulus and leaflets a more functional anatomic shape and tension. The more functional anatomic shape and tension are conducive to coaptation of the leaflets, which, in turn, reduces retrograde flow or regurgitation. In some embodiments, the implant is configured to rest at or near a heart valve annulus and apply a direct mechanical force along the minor axis of the annulus to inwardly displace tissue toward the center of the annulus. For some applications, the implant is configured to extend significantly above the plane of the valve, while for other applications, the implant is configured to extend a short distance above the plane of the valve.

U.S. Pat. No. 7,500,989 to Solem et al. describes devices and methods for treating mitral regurgitation by reshaping the mitral annulus in a heart. One device for reshaping the mitral annulus is provided as an elongate body having dimensions as to be insertable into a coronary sinus. The elongate body includes a proximal frame having a proximal anchor and a distal frame having a distal anchor. A ratcheting strip is attached to the distal frame and an accepting member is attached to the proximal frame, wherein the accepting member is adapted for engagement with the ratcheting strip. An actuating member is provided for pulling the ratcheting strip relative to the proximal anchor after deployment in the coronary sinus. In one embodiment, the ratcheting strip is pulled through the proximal anchor for pulling the proximal and distal anchors together, thereby reshaping the mitral annulus.

The following patents and patent applications may be of interest:

EP Patent EP 06/14342 to Pavcnik et al.
EP Patent EP 10/06905 to Organ
PCT Publication WO 00/22981 to Cookston et al.
PCT Publication WO 01/26586 to Seguin
PCT Publication WO 01/56457 to Pruitt
PCT Publication WO 05/046488 to Douk et al.
PCT Publication WO 06/012013 to Rhee et al.
PCT Publication WO 06/086434 to Powell et al.
PCT Publication WO 06/097931 to Gross et al.
PCT Publication WO 06/105084 to Cartledge et al.
PCT Publication WO 96/39963 to Abela et al.
PCT Publication WO 96/40344 to Stevens-Wright et al.
PCT Publication WO 97/01369 to Taylor et al.
PCT Publication WO 98/46149 to Organ
U.S. Pat. No. 3,656,185 to Carpentier
U.S. Pat. No. 4,961,738 to Mackin
U.S. Pat. No. 5,325,845 to Adair
U.S. Pat. No. 5,593,424 to Northrup III
U.S. Pat. No. 5,716,370 to Williamson, IV et al.
U.S. Pat. No. 5,855,614 to Stevens et al.
U.S. Pat. No. 6,074,401 to Gardiner et al.
U.S. Pat. No. 6,102,945 to Campbell
U.S. Pat. No. 6,619,291 to Hlavka et al.
U.S. Pat. No. 6,918,917 to Nguyen et al.
U.S. Pat. No. 6,926,730 to Nguyen et al.
U.S. Pat. No. 7,150,737 to Purdy et al.
U.S. Pat. No. 7,172,625 to Shu et al.
U.S. Pat. No. 7,175,660 to Cartledge et al.
U.S. Pat. No. 7,226,467 to Lucatero et al.
US Patent Application Publication 2003/0078465 to Pai et al.
US Patent Application Publication 2003/0199974 to Lee et al.
US Patent Application Publication 2004/0127983 to Mortier et al.
US Patent Application Publication 2004/0148021 to Cartledge et al.
US Patent Application Publication 2004/0260394 to Douk et al.
US Patent Application Publication 2005/0055038 to Kelleher et al.
US Patent Application Publication 2005/0096740 to Langberg et al.
US Patent Application Publication 2006/0095009 to Lampropoulos et al.
US Patent Application Publication 2006/0195134 to Crittenden
US Patent Application Publication 2006/0282161 to Huynh et al.
US Patent Application Publication 2006/0247763 to Slater
US Patent Application Publication 2008/0027483 to Cartledge et al.
US Patent Application Publications 2004/0148019 and 2004/0148020 to Vidlund et al.

The following articles, which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF THE INVENTION

In some embodiments of the present invention, systems and methods are provided for contracting an annuloplasty structure in order to repair a dilated mitral valve of a patient. The annuloplasty structure comprises an annuloplasty ring. The annuloplasty structure is compressible at least in part and has a lumen therethrough. A movement-restriction mechanism is disposed within the lumen of the annuloplasty structure and is selectively and actively engageable. The movement-restriction mechanism comprises a strip of flexible metal having first and second ends. The first end of the strip is moveable with respect to the second end of the strip, which is typically fixed to a housing coupled to the annuloplasty structure. At least a portion of the strip, e.g., the portion which is disposed adjacently to the first end, is shaped to provide a plurality of recesses that are engageable by a recess-engaging portion that is coupled to the housing.

Typically, the recess-engaging portion is coupled to a lever arm and the recess-engaging potion and/or the lever arm is reversibly coupled to a mechanical support which maintains a position of the recess-engaging potion with respect to the strip in which the recess-engaging portion does not engage any of the recesses of the strip. When none of the recesses are engaged by the recess-engaging portion, the first end slides freely in either direction with respect to the second end of the strip. Once the mechanical support is actively released from the recess-engaging potion and/or from the lever arm, the recess-engaging portion is positioned within one of the recesses of the strip, thereby locking in place the strip and restricting motion in either direction of the first end of the strip with respect to the second end of the strip.

The annuloplasty structure is shaped to provide a primary, outer body portion having at least a first portion comprising a material, e.g., a coil, that is longitudinally-compressible. The annuloplasty structure comprises a secondary body portion comprising a compressible element, e.g., a tubular coil, that is disposed within a lumen provided by the primary body portion. Portions of the secondary body portion are coupled to a surface of a portion of the strip of the movement-restriction mechanism. Typically, the system comprises a flexible member, e.g., a wire, that functions to compress and contract the annuloplasty structure. The flexible member is typically disposed within a lumen provided by the secondary compressible element. When the annuloplasty structure comprises an annuloplasty ring, the secondary compressible element is coupled to an outer surface of the ring-shaped strip. The secondary compressible element ensures that the flexible member is maintained at an outer perimeter of the ring-shaped strip.

The first end of the strip passively slides in a first direction with respect to the second end of the strip, in response to active pulling on first and second ends of the flexible member. That is, the first end of the strip is not pulled by the flexible member, but rather is passively pushed in response to the contracting of the flexible member. As the first end of the strip slides in the first direction with respect to the second end, and the strip contracts to assume a smaller perimeter than in its resting state, the compressible element of the primary body portion of the annuloplasty structure contacts to assume a smaller perimeter, in turn. When the flexible member is released and is allowed to relax, the first end slides in a second direction with respect to the second end, and in turn, the perimeter of the strip is enlarged and the compressible element of the body portion expands.

Thus, the selectively-engageable movement-restriction mechanism facilitates unobstructed contraction and expansion of the annuloplasty structure, and thereby unobstructed adjustment of a perimeter thereof. When a desired perimeter of the annuloplasty structure is achieved, the mechanical structure is actively released which releases recess-engaging portion such that it engages a recess of the strip, thereby locking in place the strip and restricting further contraction and expansion of the annuloplasty structure.

There is therefore provided, in accordance with some applications of the present invention, apparatus, including:

a locking mechanism;

an implant shaped so as to define a lumen therethrough; and a flexible strip disposed at least in part within the lumen, the strip shaped so as to define:
  a first end,
  a second end, and
  a plurality of recesses,
  the first and second ends coupled to the locking mechanism such that the strip defines a closed loop and a perimeter thereof which (a) shortens when the first end is advanced through the locking mechanism in a first direction thereof and (b) expands when the first end is advanced in a second direction opposite the first direction, and the locking mechanism includes:

a moveable recess-engaging portion;

a mechanical support, removably coupled to the recess-engaging portion; and a force applicator which maintains the recess-engaging portion in a position in which the recess-engaging portion is not disposed in any of the recesses and which, upon decoupling of the mechanical support from the recess-engaging portion, restricts motion of the plurality of recesses of the strip with respect to the second end of the strip, by facilitating positioning of the recess-engaging portion in one of the plurality of recesses.

In some applications, the force applicator includes a spring.

In some applications, for each one of the recesses, the strip is shaped to provide first and second opposing walls which define the recess, the first wall having a dimension that is substantially the same as a dimension of the second wall.

In some applications, the implant includes expanded polytetrafluoroethylene (ePTFE).

In some applications, the implant is coated with polytetrafluoroethylene.

In some applications, the apparatus is configured to be implanted along an annulus of a mitral valve of a patient, and the apparatus is configured to be transcatheterally advanced toward the annulus.

In some applications the apparatus includes a flexible member disposed within the lumen of the implant and alongside the strip, the flexible member being configured push against the strip to contract the strip and facilitate passive advancement of the first end of the strip through the locking mechanism.

In some applications:

the implant is configured to be implanted along an annulus of a mitral valve of a patient, the flexible member is configured to contract the implant when the flexible member is pulled, and the implant is configured to contract the annulus in response to the contraction thereof.

In some applications:

the implant includes an outer body portion shaped to define the lumen, when formed into the closed loop, the flexible strip is shaped to provide an inner surface and an outer surface, and the apparatus further includes an inner body portion coupled at at least a portion thereof to the outer surface of the strip, the inner body portion being shaped so as to define an inner body lumen therethrough.

In some applications the apparatus includes a flexible member configured for slidable advancement through the inner body lumen, the flexible member being configured to push against the strip to contract the strip and to facilitate passive advancement of the first end of the strip with respect to the second end of the strip.

In some applications, the inner body portion is compressible.

In some applications, the inner body portion includes expanded polytetrafluoroethylene (ePTFE).

In some applications:

the apparatus is configured to be implanted along an annulus of a mitral valve of a heart of a patient, a first section of the implant is flexible and longitudinally-compressible, and a second section in series with the first section of the implant, the second section being flexible and less longitudinally-compressible than the first section.

In some applications, the second section is not longitudinally-compressible.

In some applications, a radius of curvature at a center of the first section is smaller than a radius of curvature at a center of the second section, when no external force is applied to the implant.

In some applications, the second section of the implant has first and second ends thereof and a body portion disposed between the first and second ends, the second section of the implant being configured to be disposed along a portion of the annulus in a manner in which:

the first end of the second section is configured to be coupled to the annulus in a vicinity of a left trigone of the heart that is adjacent to the mitral valve of the patient, the second end of the second section is configured to be coupled to the annulus in a vicinity of a right trigone of the heart that is adjacent to the mitral valve, and the body portion is configured to be disposed along the annulus in a vicinity of the annulus that is between the left and right trigones.

In some applications, the body portion disposed between the first and second ends of the second section of the implant has a length of 10-50 mm.

There is further provided, in accordance with some applications of the present invention, a method, including:

providing an implant shaped so as to define a lumen therethrough and a flexible strip disposed at least in part within the lumen of the implant, the strip having:

a first end,
a second end, and
a plurality of recesses, and
a locking mechanism to which the first and second ends of the strip are coupled such that the strip defines a closed loop and a perimeter thereof which (a) shortens when the first end is advanced through the locking mechanism in a first direction thereof and (b) expands when the first end is
advanced in a second direction opposite the first direction;

advancing the first end of the strip in first and second opposing directions with respect to the second end of the strip;

maintaining a recess-engaging portion in a position in which the recess-engaging portion is not disposed in any of the plurality of recesses during the advancing; and restricting the advancing by facilitating active positioning of the recess-engaging portion in one of the plurality of recesses.

In some applications the method includes, coupling the implant along an annulus of a mitral valve of a patient.

In some applications the method includes, advancing the implant transcatheterally toward an annulus of a patient.

In some applications, advancing the portion of the strip in first and second opposing directions with respect to the second end of the strip includes contacting and expanding the implant, respectively.

In some applications the method includes, coupling the implant along an annulus of a mitral valve of a patient, and contacting and expanding the implant includes contacting and expanding the annulus, respectively.

There is also provided, in accordance with some applications of the present invention, apparatus, including:

an implant including a flexible longitudinal member having first and second ends that are opposable to form the longitudinal member into a closed loop having a perimeter thereof which (a) shortens when the first end is advanced in a first direction with respect to the second end in a first direction thereof and (b) expands when the first end is advanced with respect to the second end in a second direction opposite to the first direction, and when formed into the closed loop, the longitudinal member is shaped to provide an inner surface and an outer surface with respect to a center of the closed loop;

a body portion coupled at at least a portion thereof to the outer surface of the longitudinal member, body portion being shaped so as to define a lumen therethrough; and a flexible contracting member being disposed within and slidably advanceable through the lumen to facilitate a modulation of a perimeter of the body portion, which, in turn facilitates a modulation of a perimeter of the longitudinal member.

In some applications the apparatus includes, a tubular structure shaped so as to define a tubular structure lumen therethrough, and:

the flexible longitudinal member is disposed at least in part within the tubular structure lumen, and the longitudinal member is configured to facilitate a modulation of a perimeter of the tubular structure in response to the modulation of the perimeter of the longitudinal member.

In some applications, the implant includes an annuloplasty ring.

The present invention will be more fully understood from the following detailed description of embodiments thereof, taken together with the drawings, in which:

BRIEF DESCRIPTION OF THE DRAWINGS

FIGS. 2A-C are schematic illustrations of an inner compressible element disposed within a lumen of the ring structure of FIG. 1, in accordance with some embodiments of the present invention;

DETAILED DESCRIPTION OF THE EMBODIMENTS

Figure 1:
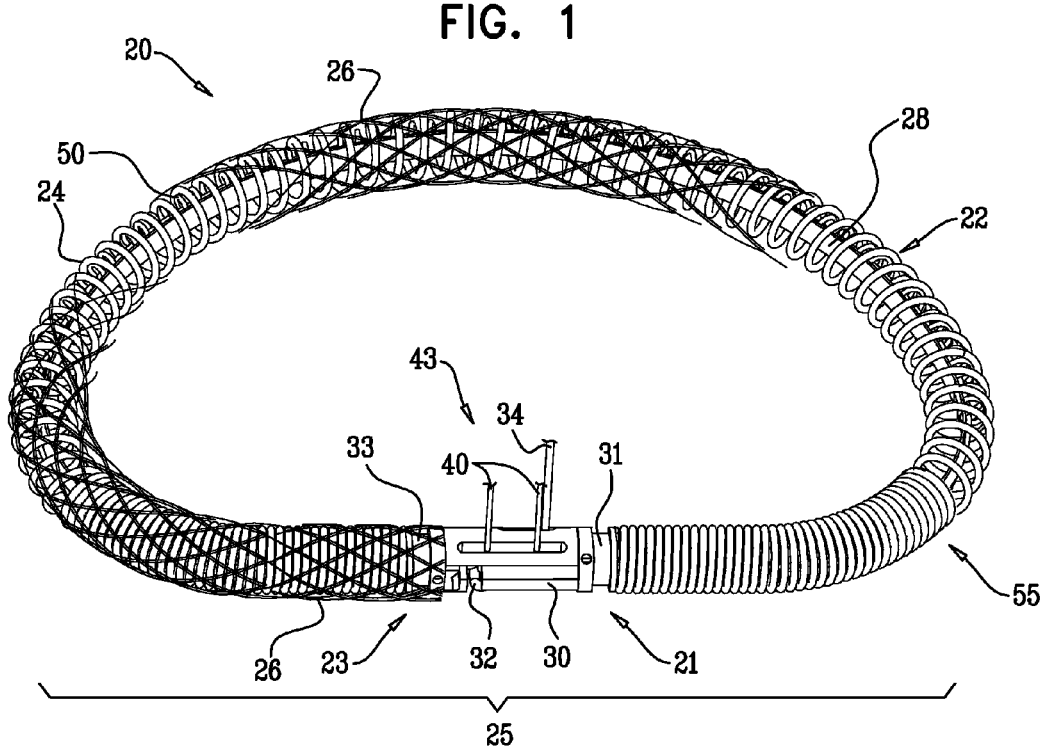
FIG. 1 is a schematic illustration of an annuloplasty ring structure, in accordance with some embodiments of the present invention.
Figure 3:
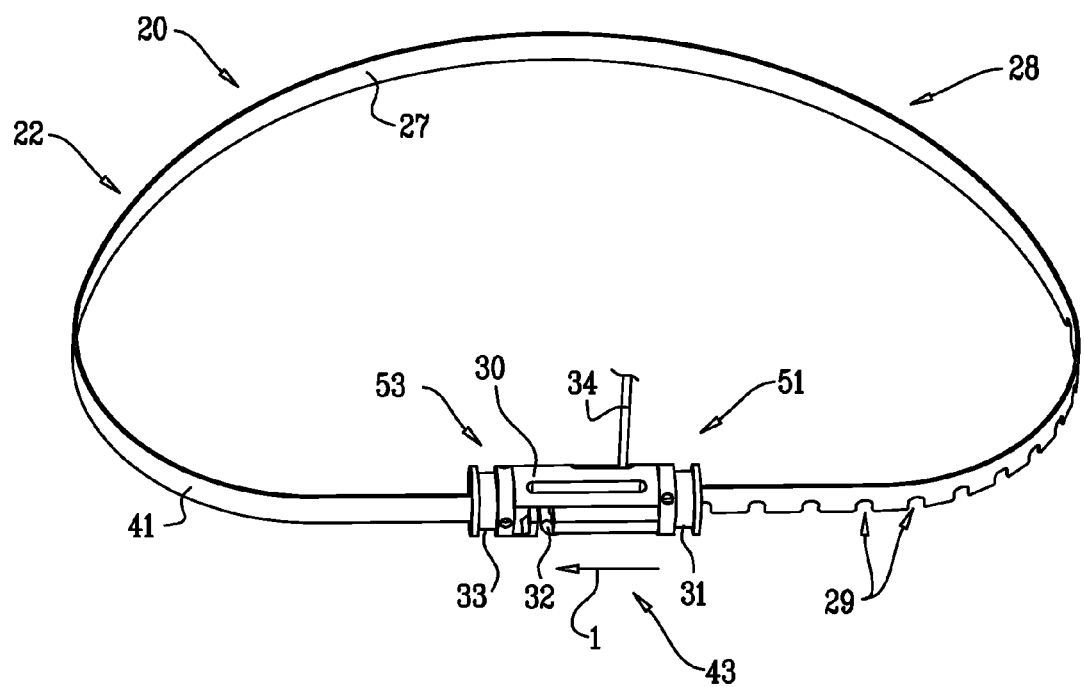
FIG. 3 is a schematic illustration of a movement-restriction mechanism comprising a strip coupled to the compressible element of FIGS. 2A-C, in accordance with some embodiments of the present invention.

Reference is now made to FIGS. 1-3, which are schematic illustrations of an annuloplasty structure 20 comprising an annuloplasty ring 22 having a tubular outer body portion 55 and a tubular inner body portion 50, and a movement-restriction mechanism comprising a flexible strip 28, in accordance with some embodiments of the present invention. Typically, strip 28 comprises a flexible longitudinal member comprising a flat band or ribbon. Outer body portion 55 comprises a compressible portion 24 and one or more less-compressible portions 25. For example, compressible portion 24 may comprise a coiled element, as shown by way of illustration and not limitation. For some applications, compressible portion 24 may comprise stent-like struts, or a braided mesh. Typically, structure 20 comprises a tubular structure defining a substantially longitudinal lumen which houses a flexible contracting member 40 and strip 28 of the movement-restriction mechanism. Typically, body portion 55 is surrounded by a braided mesh. Compressible portion 24 and the braided mesh surrounding body portion 55 are configured for the advancement therethrough of tissue anchors and/or sutures which anchor, suture, or otherwise couple structure 20 to the native annulus of the heart valve.

At least a portion of strip 28 is configured for slidable advancement within the lumen of structure 20 in response to the pulling or pushing of flexible member 40. When flexible member 40 is tightened, or pulled, the portion of strip 28 is made to slide in a first direction, and, consequently, a perimeter of strip 28 is reduced, or shortened, thereby compressing and contracting structure 20 such that a perimeter thereof is, in turn, reduced. When flexible member 40 is loosened, the portion of strip 28 is made to slide in a second direction opposite the first, and, consequently, a perimeter of strip 28 is enlarged thereby expanding structure 20 such that a perimeter thereof is, in turn, enlarged.

In addition to facilitating a modulation of the perimeter of structure 20, strip 28 functions to (a) provide a scaffold for stabilizing and maintaining the spatial configuration of structure 20 and for supporting the lumen provided by outer body portion 55, and (b) prevent crushing or collapsing of ring 22. Additionally, since strip 28 comprises nitinol (by way of illustration and not limitation), strip 28 is flexible and has elastic shape-memory to form structure 20 into a D-shaped closed configuration. It is to be noted that ring 22 may be shaped to define any suitable configuration, e.g., a saddle shape, an oval shape, an elliptical shape, etc.

Typically, a filler material (e.g., polyester, polytetrafluoroethylene (PTFE), polyethylene terephthalate (PET), or expanded polytetrafluoroethylene (ePTFE)) is packed within at least a portion, e.g., 50%, 75%, or 100%, of the lumen of outer body portion 55. The filler material functions to prevent (1) formation within the lumen provided by outer body portion 55 of clots or (2) introduction of foreign material into the lumen which could obstruct the sliding movement of strip 28 and flexible member 40.

Compressible portion 24 is compressible along a longitudinal axis of the lumen defined by structure 20. Structure 20 has first and second ends 21 and 23 which are coupled to a locking mechanism 43. Locking mechanism 43 comprises a housing 30 having first and second coupling members 31 and 33 to which are coupled, e.g., welded or otherwise fastened, to first and second ends 21 and 23, respectively, of structure 20. Housing 30 facilitates (a) the advancement, in either direction, of a first end of strip 28 with respect to a second end of strip 28, and (b) selective, active locking of strip 28 with respect to housing 30.

Flexible member 40 comprises a flexible and/or super-elastic material, e.g., nitinol, polyester, stainless steel, or cobalt chrome, and is configured to reside permanently within structure 20. In some embodiments, flexible member 40 comprises a braided polyester suture (e.g., Ticron). In some embodiments, flexible member 40 is coated with polytetrafluoroethylene (PTFE). In some embodiments, flexible member 40 comprises a plurality of wires that are intertwined to form a rope structure.

FIG. 1 shows an assembly of components shown in FIGS. 2A-C and 3. As shown in FIG. 1, structure 20 comprises compressible portion 24 and less-compressible portion 25, which is less longitudinally-compressible than portion 24, e.g., not longitudinally-compressible. Typically, compressible portion 24 and less-compressible portion 25 are surrounded by a braided mesh 26 (for clarity of illustration, portions of ring 22 are shown as not being surrounded by mesh 26). Typically, braided mesh 26 comprises a flexible material, e.g., metal or fabric such as polyester, and is longitudinally-compressible.

Typically, compressible portion 24 and less-compressible portion 25 comprise a flexible, biocompatible material, e.g., nitinol, stainless steel, platinum iridium, titanium, expanded polytetrafluoroethylene (ePTFE), or cobalt chrome. For some applications, portions 24 and 25 are coated with PTFE (Polytetrafluoroethylene). In some embodiments, compressible portion 24 comprises accordion-like compressible structures (configuration not shown) which facilitate proper cinching of the annulus when structure 20 is contracted. Longitudinal compression of compressible portion 24 enables portions of annuloplasty ring 22 to contract and independently conform to the configuration of the annulus of the mitral valve of a given patient. Thus, since structure 20 is sutured or otherwise anchored to the annulus, the compression of compressible portion 24 facilitates the contraction of structure 20, and responsively thereto, the contraction of the annulus.

Structure 20 defines a substantially ring-shaped configuration, e.g., a "D"-shaped configuration, as shown, which conforms to the shape of the annulus of a mitral valve of the patient. Prior to the contracting of structure 20, compressible portion 24 is relaxed and structure 20 defines a first perimeter thereof. Portion 25 is configured to be disposed along the fibrous portion of the annulus that is between the trigones of the mitral valve of the heart when structure 20 is anchored, sutured, fastened or otherwise coupled to the annulus of the mitral valve. Less-compressible portion 25 imparts rigidity to structure 20 in the portion thereof that is disposed between the fibrous trigones such that structure 20 mimics the conformation and functionality of the mitral valve. Typically, portion 25 has a length of 10-50 mm. Additionally, during contraction of structure 20 responsively to the pulling of flexible member 40, less-compressible portion 25 minimizes the need for additional compression forces on the portions of structure 20 which lie adjacently to portions of the native annulus which do not need to be and/or cannot be contracted.

Thus, structure 20 defines a compressible portion and a less-compressible portion. Typically, a radius of curvature at a center of compressible portion 24 is less than a radius of curvature at a center of less-compressible portion 25, when no external force is applied to annuloplasty structure 20.

It is to be noted that compressible portion 24 and less-compressible portion 25 comprise coiled elements by way of illustration and not limitation. For example, compressible portion 24 and less-compressible portion 25 may comprise stent-like struts, or a braided mesh. In either configuration, portion 25 is permanently longitudinally compressed when ring 22 is in a resting state.

Reference is now made to FIGS. 2A and 3. FIG. 2A shows inner body portion 50 and strip 28 of structure 20, in accordance with some embodiments of the present invention. For clarity of illustration, structure 20 is shown without surrounding outer body portion 55 (as illustrated hereinabove with reference to FIG. 1). Typically, inner body portion 50 and strip 28 are disposed within the lumen provided by outer body portion 55. Strip 28 comprises a flexible material, e.g. nitinol, and has first and second ends 51 and 53 which are opposable to form strip 28 into a substantially closed loop, ring-shaped configuration. Typically, second end 53 of strip 28 is coupled to locking mechanism 43 by being fixed to housing 30, while first end 51 of strip 28 is dynamic and is advanceable in either direction with respect to second end 53. That is, first end 51 is reversibly coupled to locking mechanism 43. When both first and second ends 51 and 53 are coupled to locking mechanism 43, strip 28 is formed into a closed loop. Strip 28 is shaped to provide a recesses portion 129 which is shaped to define a plurality of recesses 29. Typically, recesses portion 129 is provided adjacent to first end 51 of strip 28, as shown by way of illustration and not limitation. It is to be noted that recesses portion 129 may be provided at any suitable location along strip 28. As shown in FIG. 3, the opposing walls on either side of each recess 29 (i.e., the walls that define recess 29) have substantially the same height and angle, i.e., 90 degrees with respect to the longitudinal axis of structure 20, as shown.

Reference is again made to FIG. 2A. A portion of flexible member 40 surrounds strip 28 along an outer perimeter of the strip. Housing 30 of locking mechanism 43 is shaped to define at least one opening through which first and second portions of flexible member 40 emerge from structure 20. Typically, the first and second portions of flexible member 40 extend to a site outside the body of the patient. In response to a pulling force applied to one or both of first and second portions of flexible member 40, the portion of flexible member 40 that surrounds strip 28 contracts. In response to the contraction, flexible member 40 applies a force to and pushes against strip 28, thereby contracting strip 28. As the force is applied to strip 28 by flexible member 40, first end 51 of strip 28 slides with respect to second end 53 of strip 28, as indicated by an arrow 1, thereby reducing a perimeter of strip 28 and ring 22. As the perimeter of ring 22 is reduced, compressible element 24 contracts longitudinally and facilitates radial contraction of ring 22.

Strip 28, when formed into a substantially ring-shaped configuration, provides an inner surface 27 and an outer surface 41 with respect to a center of the ring-shaped, closed-loop configuration of strip 28 and ring 22. Inner body portion 50 is typically welded, or otherwise coupled, at respective locations to outer surface 41 of strip 28 (as shown in FIGS. 2A-C). Inner body portion 50 comprises a compressible material, e.g., nitinol, stainless steel, platinum iridium, titanium, expanded polytetrafluoroethylene (ePTFE), or cobalt chrome. In some embodiments, inner body portion 50 is coated with PTFE (polytetrafluoroethylene). Inner body portion 50 is shaped to define a plurality of coils, by way of illustration and not limitation. For some applications, inner body portion 50 may comprise accordion-like compressible structures (configuration not shown). In some embodiments, outer and inner body portions 55 and 50 are shaped to define a tubular structure comprising a compressible material, e.g., ePTFE. In response to the contracting of outer body portion 55 of structure 20: (1) the perimeter of outer body portion 55 is reduced such that outer body portion 55 pushes against strip 28, (2) in response to the pushing of strip 28, the first end of the strip slides in with respect to the second end of the strip such that the perimeter of strip is reduced, and (3) in response to the contracting of the strip, the inner body portion 50 contracts.

FIG. 2C shows a portion of strip 28, inner body portion 50, and flexible member 40 at a cross-section of strip 28, inner body portion 50, and flexible member 40, as shown in FIG. 2B. As shown in FIG. 2C, inner body portion 50 is shaped to provide a lumen for slidable advancement therethrough of a portion of flexible member 40. Because flexible member 40 is housed in the lumen of inner body portion 50, the flexible member remains disposed along outer surface 41, i.e., at an outer perimeter of strip 28, and is restricted from sliding above or below strip 28 and toward inner surface 27, i.e., an inner perimeter of strip 28. Such a configuration ensures that flexible member 40 remains disposed along outer surface 41 of strip 28 such that flexible member 40, in response to a pulling force applied thereto, appropriately applies a contraction force to strip 28.

Flexible member 40, by being disposed within and slidably advanceable through the lumen of inner body portion 50, facilitates a modulation of a perimeter of inner body portion 50, which, in turn facilitates a modulation of a perimeter of strip 28, and ultimately, outer body portion 55.

Figure 4:
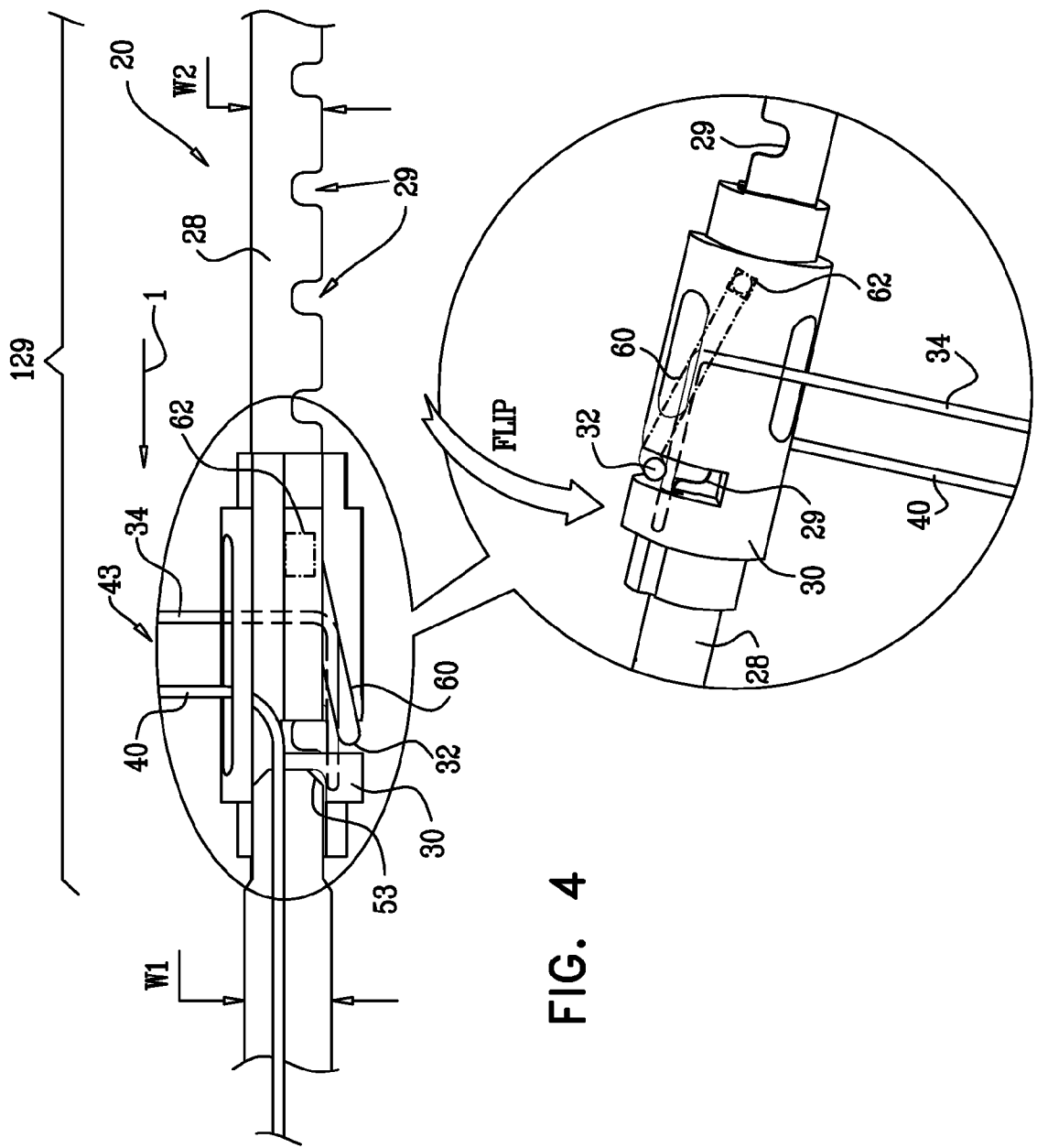
FIG. 4 is a schematic illustration of a locking mechanism to lock a configuration of the strip of FIG. 3, in accordance with some embodiments of the present invention.

Reference is now made to FIG. 4, which shows locking mechanism 43 of structure 20 comprising housing 30 and a motion restrictor 60 which is actively engageable by a mechanical support 34, in accordance with some embodiments of the present invention. Motion restrictor 60 comprises a recess-engaging portion 32 that is coupled to a lever arm, which, in turn, is coupled to housing 30 by a force applicator 62. Typically, force applicator 62 comprises a mechanical spring, by way of illustration and not limitation, which causes motion of recess-engaging portion 32 with respect to housing 30. Force applicator 62 creates a tendency for the lever arm and recess-engaging portion 32 to assume a position in which recess-engaging portion 32 engages one of recesses 29 of strip 28. In order to restrict such a tendency, locking mechanism 43 comprises a mechanical support 34 which maintains recess-engaging portion 32 in a position in which recess-engaging portion 32 does not engage any of recesses 29. Mechanical support 34 comprises a flexible rod or string which is (a) removably coupled at a first end thereof to housing 30, and (b) accessible by an operating physician at a second end thereof. Support 34 comprises a portion adjacent to the first end of the support which functions to block recess-engaging portion 32 from engaging any of recesses 29. That is, recess-engaging portion 32 rests against the portion of support 34.

Typically, recesses portion 129 of strip 28 is narrower than the rest of the portions of strip 28. That is, strip 28 has a width W1 of 1.6-1.9 mm, e.g., 1.6 mm while recesses portion 129 has a width W2 of within the lumen provided by primary body portion 55 1.2-1.5 mm, e.g., 1.3 mm. Width W2 of recesses portion 129 allows recesses portion 129 to slide along inner surface 27 of a portion of strip 28 adjacent to second end 53, while not being obstructed by the inner wall of outer body portion 55 which surrounds the lumen of outer body portion 55.

Figure 5:
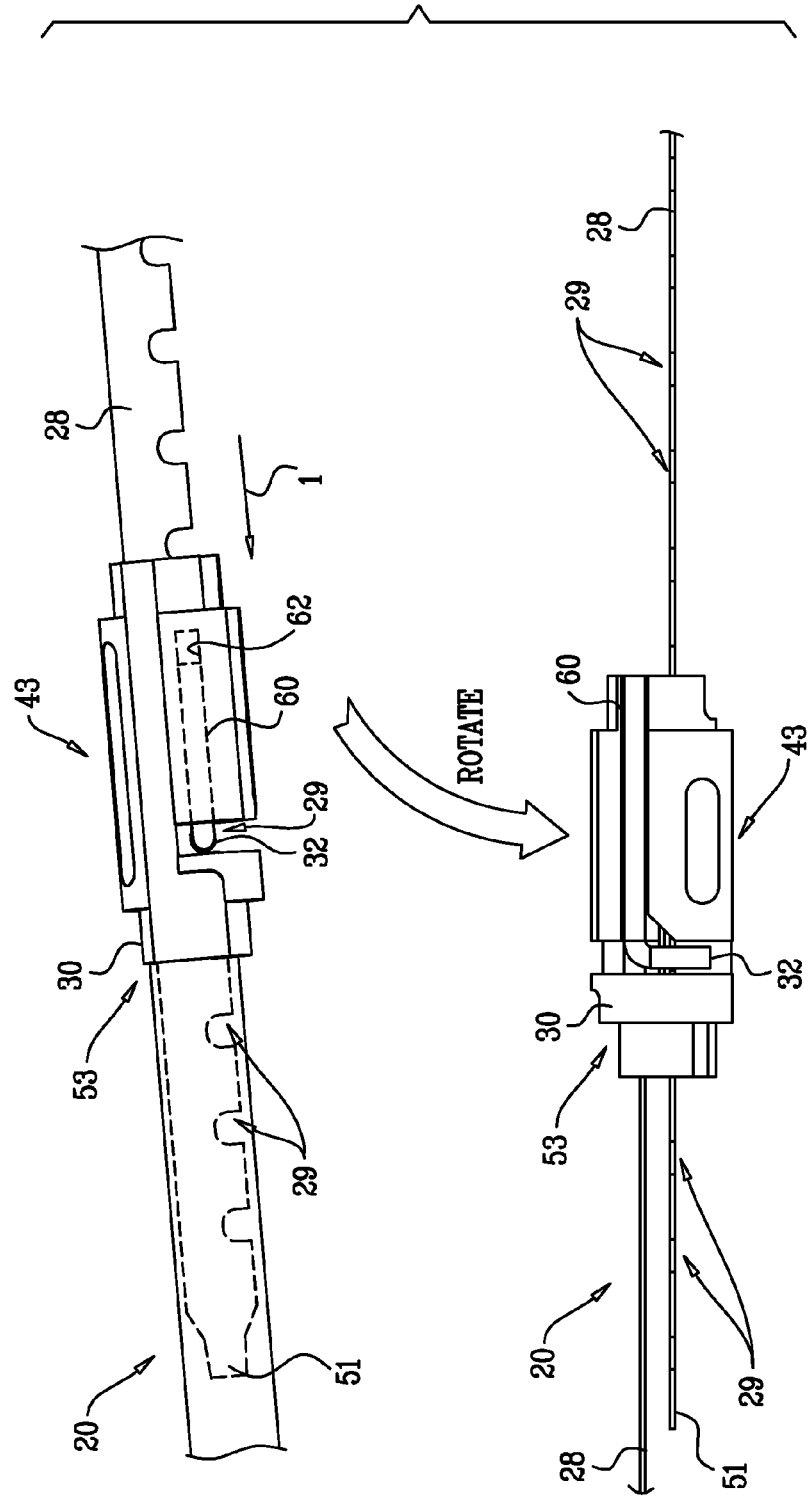
FIG. 5 is a schematic illustration of the locking mechanism in a locked state, in accordance with some embodiments of the present invention.

In such a configuration, first end 51 of strip 28 may be advanced bidirectionally with respect to second end 53 of strip 28 and housing 30, and thereby facilitates contraction and expansion of structure 20 in order to control the perimeter of structure 20. Once the physician achieves a desired perimeter length of structure 20, the physician actively and selectively engages locking mechanism 43. By pulling on mechanical support 34 from a site outside the body of the patient, the first end of support 34 is disengaged and removed from housing 30, thereby allowing recess-engaging portion 32 to engage one of recesses 29, as shown in FIG. 5.

As shown in FIGS. 2A, 3, 4, and 5, second end 53 of strip 28 is fixed to housing 30 in a vicinity of recess-engaging portion 32. In some embodiments, a flexible, curved secondary scaffold portion (not shown) is coupled to housing 30 in a vicinity of housing 30 that is opposite to second end 53 of strip 28 (i.e., the side of housing 30 through which first end 51 of strip 28 is introduced within housing 30 and slides therethrough) and extends away from housing 30. The secondary scaffold portion is disposed within outer body portion 55 and has a dimension of between 50 and 120 degrees of structure 20 in its closed loop configuration. In some embodiments, the secondary scaffold portion has a dimension that is substantially equal to or less than the dimension of recesses portion 129. The secondary scaffold portion may be shaped to define a strip, a tube, or a rod, and comprises a flexible material, e.g., nitinol, which provides a balancing force to structure 20 as first end 51 of strip 53 is advanced beyond housing 30 and away from the secondary scaffold portion.

In some embodiments of the present invention, the contraction of strip 28 and thereby structure 20 is reversible. In other words, releasing flexible member 40 following its tightening, slackens the portion of flexible member 40 surrounding strip 28. Responsively, annuloplasty structure 20 gradually relaxes (i.e., with respect to its contracted state) as the compressible portions of outer body portion 55 and inner body portion 50 gradually expand. As the compressible portions expand, first end 51 of strip 28 slides with respect to second end 53 in the direction opposite that in which it is slid during contraction of structure 20.

It is to be noted that for some embodiments, second end 53 of strip 28 is not fixed to ring 22. For example, both first and second ends 51 and 53 of strip 28 may be configured for slidable advancement through the lumen of structure 20. That is, first and second ends 51 and 53 of strip 28 may be advanceable with respect to each other in opposite directions.

FIG. 5 shows locking mechanism 43 locking strip 28 in place, in accordance with some embodiments of the present invention. The lower illustration of FIG. 5 shows a 90 degree flip along a y-axis of the upper image of FIG. 5. Once the physician determines that the annuloplasty ring structure has assumed a desired perimeter, the physician pulls on mechanical support 34, as described hereinabove with reference to FIG. 4. Mechanical support 34 is pulled away from housing 30 of locking mechanism 43 which allows for the lever arm of motion restrictor 60 to pivot along force applicator 62 such that motion restrictor 60 assumes a configuration in which (1) the lever arm of motion restrictor 60 lies in parallel with a longitudinal axis of housing 30, and (2) recess-engaging portion 32 is disposed within one of recesses 29 of strip 28, as shown in FIG. 5.

Once recess-engaging portion 32 is disposed within recess 29, motion of the first end 51 of strip 28 with respect to the second end 53 of strip 28 is restricted and a perimeter of ring 22 is locked in place and maintained.

In an embodiment of the present invention, following initial implantation and adjustment of the perimeter of ring 22, the perimeter of ring 22 may be later adjusted by a tool which lifts the lever arm of motion restrictor 60 such that recess-engaging portion 32 is no longer disposed within recess 29 and, thereby locking mechanism 43 is unlocked. Once recess 29 is free of recess-engaging portion 32, a portion of strip 28 adjacent to first end 51 thereof is allowed to slide with respect to housing 30. In some embodiments, a string is permanently coupled to recess-engaging portion 32 or to the lever arm of motion restrictor 60. Following initial implantation and adjustment of ring 22, a portion of the string is accessible from outside of ring 22, and by pulling on the string, the lever arm of motion restrictor 60 is lifted, thereby unlocking locking mechanism 43 by lifting recess-engaging portion 32 away from recess 29.

Figure 6:
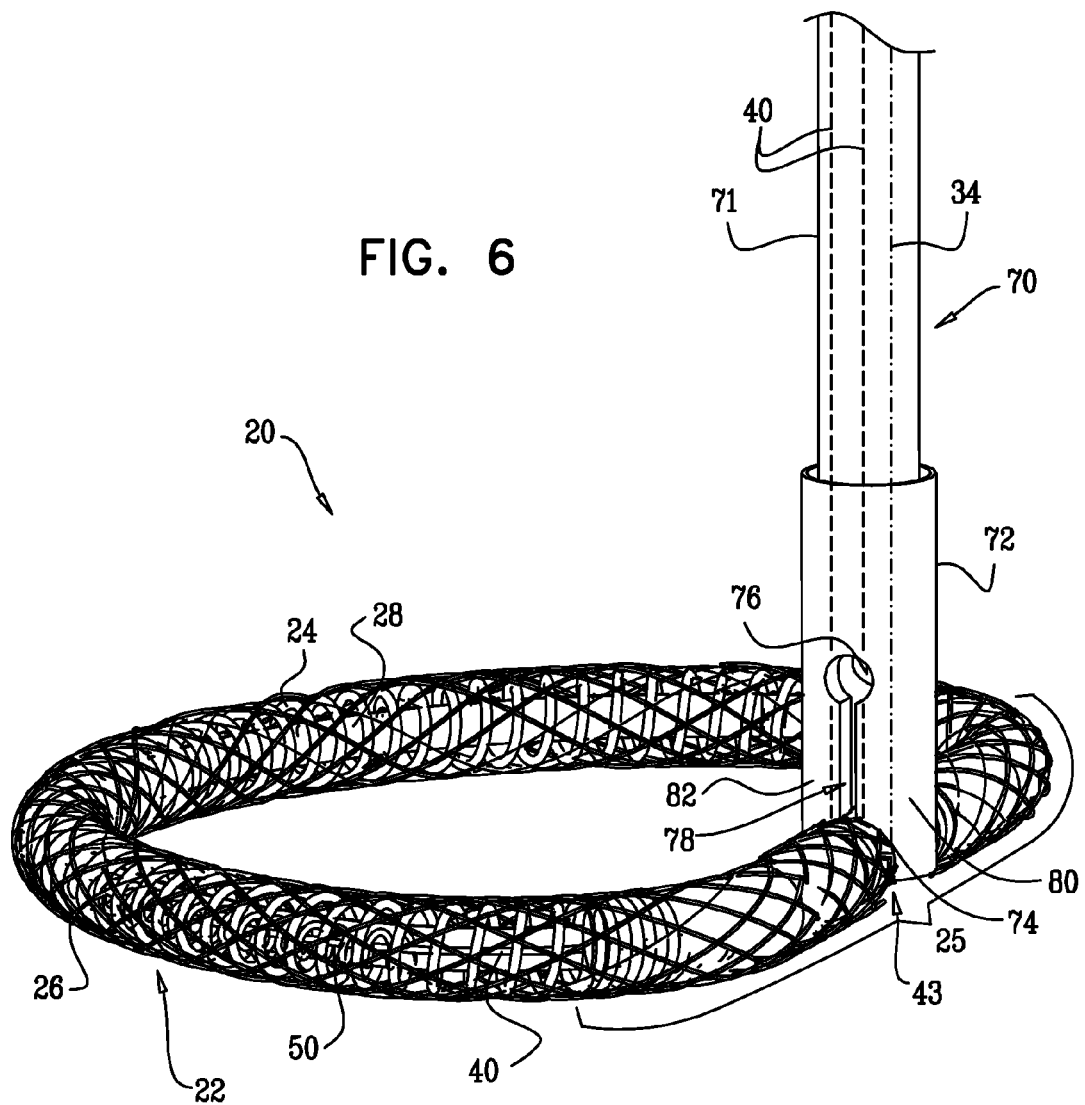
FIG. 6 is a schematic illustration of the annuloplasty ring structure of FIG. 1 being coupled to a delivery tool, in accordance with some embodiments of the present invention.

Reference is now made to FIG. 6, which is a schematic illustration of structure 20, in which ring 22 is removably coupled to a delivery tool 70, in accordance with some embodiments of the present invention. Delivery tool 70 is shaped to provide a body portion 71 having a lumen for slidable advancement therethrough of the first and second portions of flexible member 40 and of mechanical support 34. Respective ends of flexible member 40 and of mechanical support 34 are accessible from a proximal end of tool 70, i.e., the handle portion of tool 70. In some embodiments, the ends of flexible member 40 and of mechanical support 34 are exposed at the proximal end of tool 70. In some embodiments, respective ends of flexible member 40 and of mechanical support 34 are coupled to mechanical manipulators, e.g., knobs and gears, at the proximal end of tool 70. The mechanical manipulators facilitate the pulling and/or relaxing of flexible member 40 and of mechanical support 34.

A distal portion of the body portion of tool 70 is coupled to a grasper tube 72. Grasper tube 72 comprises a flexible resilient material, e.g., nitinol. Grasper tube 72 is shaped to define respective slits 78 on opposing surfaces of tube 72 which run in parallel with a longitudinal axis of tool 70, and perpendicular with respect to a plane of ring 22 coupled to tool 70. Both slits 78 on the opposing surfaces of grasper tube 72 define first and second opposing distal portions 80 and 82 of tube 72. Each of first and second distal portions 80 and 82 of tube 72 is shaped to define a curved distal surface 74 which comes in contact with an external surface of housing 30 of locking mechanism 43. It is to be noted, however, that tube 72 may be coupled to any portion along ring 22. Curved surfaces 74 are shaped such that they cup housing 30 at respective surface thereof. Tube 72 is shown in a resting state thereof in which surfaces 74 cup housing 30 of locking mechanism 43 and the distal opposing portions 80 and 82 of tube 72 are aligned along the longitudinal axis of tool 70.

During decoupling of tool 70 from structure 20, the physician pulls on tool 70 such that surfaces 74 of portions 80 and 82 slide along the external convex surfaces provided by housing 30 and are thereby pushed radially away from housing 30. In other words, during decoupling of tool 70, the distal opposing portions are pushed angularly away from the longitudinal axis of tool 70 as tool 70 is pulled proximally away from ring 22. In response to the radial expanding of the distal portions of tube 72, tool 70 is decoupled from ring 22.

Tube 72 is shaped to define respective openings 76 at the proximal end of slits 78. Openings 76 facilitate radial angular displacement and expansion of the first and second distal portions 80 and 82 of tube 72.

The length and flexibility of tool 70 depends on the procedure used to implant ring 22 along the annulus. For embodiments in which ring 22 is positioned using open-heart or minimally-invasive procedures, the delivery tool may be shorter and more rigid than a delivery tool used to facilitate advancement and implantation of ring 22 in transcatheter procedures.

Following the adjustment of structure 20 and the contraction of the valve annulus, tool 70 is removed and flexible member 40 is pulled from within the lumen of inner body portion 50 and away from ring 22 leaving ring 22 implanted along the annulus and independent of flexible member 40.

For some applications, distal portions 80 and 82 are radially-expandable. During delivery of structure 20 toward the native heart valve, distal portions 80 and 82 are disposed within a slidable overtube that compresses distal portions 80 and 82. Following the adjustment of structure 20 and the contraction of the valve annulus, the overtube is slid proximally to expose distal portions 80 and 82. Responsively, distal portions 80 and 82 expand radially, and thereby decouple tool 70 from structure 20.

It is to be noted that housing 30 of locking mechanism 43 is shown in a vicinity of less-compressible portion 25 by way of illustration and not limitation. For example, housing 30 of locking mechanism 43 may be coupled to ring 22 along any suitable location thereof, e.g., in a vicinity of compressible portion 24 of outer body portion 55. For embodiments in which housing 30 is coupled to ring 22 in a vicinity of compressible portion 24 of outer body portion 55, following implantation of ring 22, housing 30 will be disposed with respect to the annulus of the patient along a portion thereof that is not between the trigones.

Reference is now made to FIGS. 1-6. Systems and annuloplasty structures described herein may be use in surgical procedures such as open-heart, minimally-invasive, or transcatheter procedures. For embodiments in which the annuloplasty structure is advanced toward the annulus in a transcatheter procedure, the annuloplasty structure may be folded, or otherwise compressed within a catheter used to advance the annuloplasty structure toward the valve. During open-heart, minimally-invasive, or transcatheter procedures, prior to advancement of the annuloplasty structure to the annulus, a plurality of sutures are sutured (e.g., during open-heart procedures), anchored, or otherwise coupled to the annulus. The sutures are then threaded through portions of the annuloplasty structure and facilitate advancement of the annuloplasty structure along the sutures and toward the annulus. Once positioned on the annulus, the sutures are locked in place, e.g., by a bead or by being tied, with respect to the annuloplasty structure, thereby locking in place the annuloplasty structure with respect to the annulus. For embodiments in which the annuloplasty structure is coupled to the annulus during an open-heart procedure, the structure may be first positioned along the annulus prior to being anchored thereto, e.g., by suturing the structure to the annulus, or by advancing anchors with respect to the structure and into tissue of the annulus.

Reference is again made to FIGS. 1-6. It is to be noted that, in some embodiments, ring 22 does not comprise less-compressible portion 25. For example, ring 22 may comprise only compressible material as described hereinabove with reference to FIG. 1 with respect to compressible portion 24.

Reference is yet again made to FIGS. 1-6. It is to be noted that strip 28 is used by way of illustration and not limitation. Alternatively to a strip, a tubular longitudinal element may be used and is shaped to provide a plurality of recesses that are engageable by locking mechanism 43.

Reference is again made to FIGS. 1-6. It is to be noted that inner body portion 50 is shown as comprising an elongate coil by way of illustration and not limitation. Alternatively, a plurality of short distinct tubular elements may be welded or otherwise coupled at respective portions thereof to outer surface 41 of strip 28, and each tubular element is shaped so as to provide a lumen for passage therethrough of flexible member 40. Further alternatively, a plurality of rings may be welded to the outer surface of strip 28 and function as a guide to support flexible member 40 at outer surface 41 of strip 28. It is to be noted that inner body portion 50 may be shaped to define any suitable shape in cross-section, e.g., circular, rectangular, square, oval, elliptical, triangular, semi-circular, partially-elliptical.

It is to be further noted that systems described herein for treatment of dilated mitral valves may be used to treat valves other than the mitral valve, mutatis mutandis. For example, structure 20 may be used to treat an aortic valve, a pulmonary valve, or a tricuspid valve of the patient. In some embodiments, systems described herein for use with a dilated annulus may be applied in order to treat dilated venous valves.

It is to be still further noted that systems described herein for treatment of mitral valves may be used to treat other annular muscles within the body of the patient. For example, the systems described herein may be used in order to treat a sphincter muscle within a stomach of the patient.

The techniques described herein may be performed in combination with techniques described in U.S. patent application Ser. No. 11/950,930 to Gross et al., filed Dec. 5, 2007, entitled, "Segmented ring placement," which is assigned to the assignee of the present patent application and is incorporated herein by reference.

Additionally, techniques described herein may be performed in combination with techniques described in one or more of the following patent application, all of which are incorporated herein by reference:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007;

U.S. patent application Ser. No. 11/950,930 to Gross et al., entitled, "Segmented ring placement," filed on Dec. 5, 2007, which published as US Patent Application Publication 2008/0262609;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009

U.S. patent application Ser. No. 12/437,103 to Zipory et al., entitled, "Annuloplasty ring with intra-ring anchoring," filed on May 7, 2009;

PCT Patent Application PCT/IL2009/000593 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Aug. 27, 2009;

U.S. patent application Ser. No. 12/608,316 to Miller et al., entitled, "Tissue anchor for annuloplasty ring," filed on Oct. 29, 2009;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009;

U.S. patent application Ser. No. 12/689,635 to Zipory et al., entitled, "Over-wire rotation tool," filed on Jan. 19, 2010; and/or U.S. patent Ser. No. 12/689,693 to Hammer et al., entitled, "Application Deployment techniques for annuloplasty ring," filed on Jan. 19, 2010.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
providing an implant:
shaped so as to define a lumen therethrough and a flexible strip disposed at least in part within the lumen of the implant, the strip having:
a first end,
a second end, and
a plurality of recesses, and
including a locking mechanism to which the first and second ends of the strip are coupled such that the strip defines a closed loop and a perimeter thereof which (a) shortens when the first end is advanced through the locking mechanism in a first direction and (b) expands when the first end is advanced in a second direction opposite the first direction;
advancing the first end of the strip in first and second opposing directions with respect to the second end of the strip;
maintaining a recess-engaging portion in a position in which the recess-engaging portion is not disposed in any of the plurality of recesses during the advancing; and
restricting the advancing by facilitating active positioning of the recess-engaging portion in one of the plurality of recesses.

2. The method according to claim 1, further comprising coupling the implant along an annulus of a mitral valve of a patient.

3. The method according to claim 1, further comprising advancing the implant transcatheterally toward an annulus of a patient.

4. The method according to claim 1, wherein advancing the portion of the strip in first and second opposing directions with respect to the second end of the strip comprises contacting and expanding the implant, respectively.

5. The method according to claim 4, further comprising coupling the implant along an annulus of a mitral valve of a patient, and wherein contacting and expanding the implant comprises contacting and expanding the annulus, respectively.

* * * * *